US006684886B1

(12) United States Patent
Alleyne

(10) Patent No.: US 6,684,886 B1
(45) Date of Patent: Feb. 3, 2004

(54) INTERVERTEBRAL DISC REPAIR METHODS AND APPARATUS

(75) Inventor: Neville Alleyne, La Jolla, CA (US)

(73) Assignee: Prospine, Inc., San Diego, CA (US)

( * ) Notice: Subject to any disclaimer, the term of this patent is extended or adjusted under 35 U.S.C. 154(b) by 42 days.

(21) Appl. No.: 09/767,022

(22) Filed: Jan. 22, 2001

Related U.S. Application Data

(60) Provisional application No. 60/177,525, filed on Jan. 21, 2000.

(51) Int. Cl.[7] ............................................... A61B 19/00
(52) U.S. Cl. ........................................... 128/898; 607/1
(58) Field of Search ........................... 128/898; 606/15, 606/14; 607/1

(56) References Cited

U.S. PATENT DOCUMENTS

| 3,769,963 | A | * | 11/1973 | Goldman et al. | ............ | 600/476 |
| 3,788,318 | A |   | 1/1974  | Kim et al.     | ............. | 604/164.03 |
| 5,035,232 | A |   | 7/1991  | Lutze et al.   | ................. | 600/213 |
| 5,520,611 | A |   | 5/1996  | Rao et al.     | .................... | 600/245 |
| 5,552,452 | A | * | 9/1996  | Khadem et al.  | ............... | 522/63 |
| 5,902,231 | A | * | 5/1999  | Foley et al.   | ................. | 600/102 |
| 5,904,681 | A |   | 5/1999  | West           | ........................... | 606/41 |
| 5,961,499 | A |   | 10/1999 | Bonutti et al. | .............. | 604/272 |

OTHER PUBLICATIONS

Yeung, "Classification Of Annular Tears: A Critical Prospective Study In The Surgical Treatment Of The Various Types Of Tears" Jan. 14, 1999, http://www.sciatica.com/articles/annular_tears.html.*

* cited by examiner

Primary Examiner—Corrine McDermott
Assistant Examiner—Thomas Barrett
(74) Attorney, Agent, or Firm—Knobbe Martens Olson & Bear LLP

(57) ABSTRACT

Minimally invasive spinal surgery techniques include expanding an incision with an expanding cannula, inserting a retractor for retracting a nerve root, and inserting a thermal probe for repairing the annulus. A light absorbing dye may be applied to the annulus for localized heating.

5 Claims, 1 Drawing Sheet

INTERVERTEBRAL DISC REPAIR METHODS AND APPARATUS

CROSS REFERENCE TO RELATED APPLICATIONS

This application claims priority under 35 U.S.C. §119(e) to U.S. Provisional Patent Application Serial No. 60/177,525, entitled "Intervertebral Disc Repair Methods and Apparatus", filed on Jan. 21, 2000.

DESCRIPTION OF THE RELATED ART

Spinal discs comprise a central region called the nucleus pulposus surrounded by a second region known as the annulus fibrosis. The annulus portion comprises collagen fibers which may weaken, rupture, or tear, which limits annular confinement of the nucleus, producing disc bulges, herniations and other disc pathologies that cause nerve irritation or damage with resultant back pain and/or weakness and pain in the extremities.

In some open surgical treatment protocols, disc repair is attempted by removal of all or part of the damaged disc. Disc pathologies have also been treated with the application of heat to the disc. One such method is described in U.S. Pat. No. 5,433,739 to Sluijter et al. The method described in this document attempts to destroy or alter nerves at the disc surface by application of RF or direct current electrical energy to the center of the disc so as to heat the entire disc. Other approaches to heat based disc repair involve the heat induced shrinkage of the annulus fibrosis collagen. One instrument for performing such a treatment is described in U.S. Pat. Nos. 5,569,242 and 5,458,596 to Lax et al.

Existing methods of disc repair either ignore pathologies which are the true cause of patient pain and discomfort, or are apt to cause damage to the disc itself and/or adjacent structures. Improvements in disc repair methods and apparatus are thus needed.

SUMMARY

The invention comprises methods of repairing intervertebral disc tears and fissures in a minimally invasive manner. In one embodiment, one or more expanding cannulas are used to access the desired disc so as to achieve direct visualization of the disc pathology. Fiber optics may be used to illuminate the field. In one embodiment method according to the invention comprises applying heat to a disc fissure while adjacent structures such as the nerve root and thecal sac are retracted away from the site. This minimizes thermal damage to tissues adjacent to the disc during the heating process. In an especially advantageous embodiment, the disc at the fissure is heated by placing a light absorbing dye such as indigo carmen or methylene blue in and around the fissure. Directing light from, for example, a laser light source, to the dye selectively heats the dye and thus the region of the fissure without affecting or damaging other parts of the disc such as the cartilaginous end plate. With direct visualization of the area, not only disc pathologies but bony and ligamentous pathologies can be addressed at the same time.

Although the posterior approach with fiber optic illumination is advantageous because the posterior section of the disc is the site of tears or fissures for most disc pathologies, visualization of fissures can also be obtained in an anterior or retroperitoneal approach with ultrasound imaging or imaging with optical coherence tomography.

Instrumentation for performing these methods is also provided. A high speed burr with a non-conductive foot plate for retraction can be guided to the site through the cannula and used to perform an internal laminoplasty, foraminotomy, or partial fasciectomy. Other instrumentation includes a nerve root retractor which is expandable in a cephalad and caudal direction by using a trigger on the handle. The retractor may have an angulating tip and an anchoring spike for hands free retraction. The retractor may also be provided with a lumen for suction and/or a lumen for fiber optic illumination. The retractor is preferably provided with a thermally and electrically nonconducting tip to avoid heat or electrical energy transfer from the fissure site to retracted tissues during the process of heating an annular fissure.

DETAILED DESCRIPTION

Figure 1:
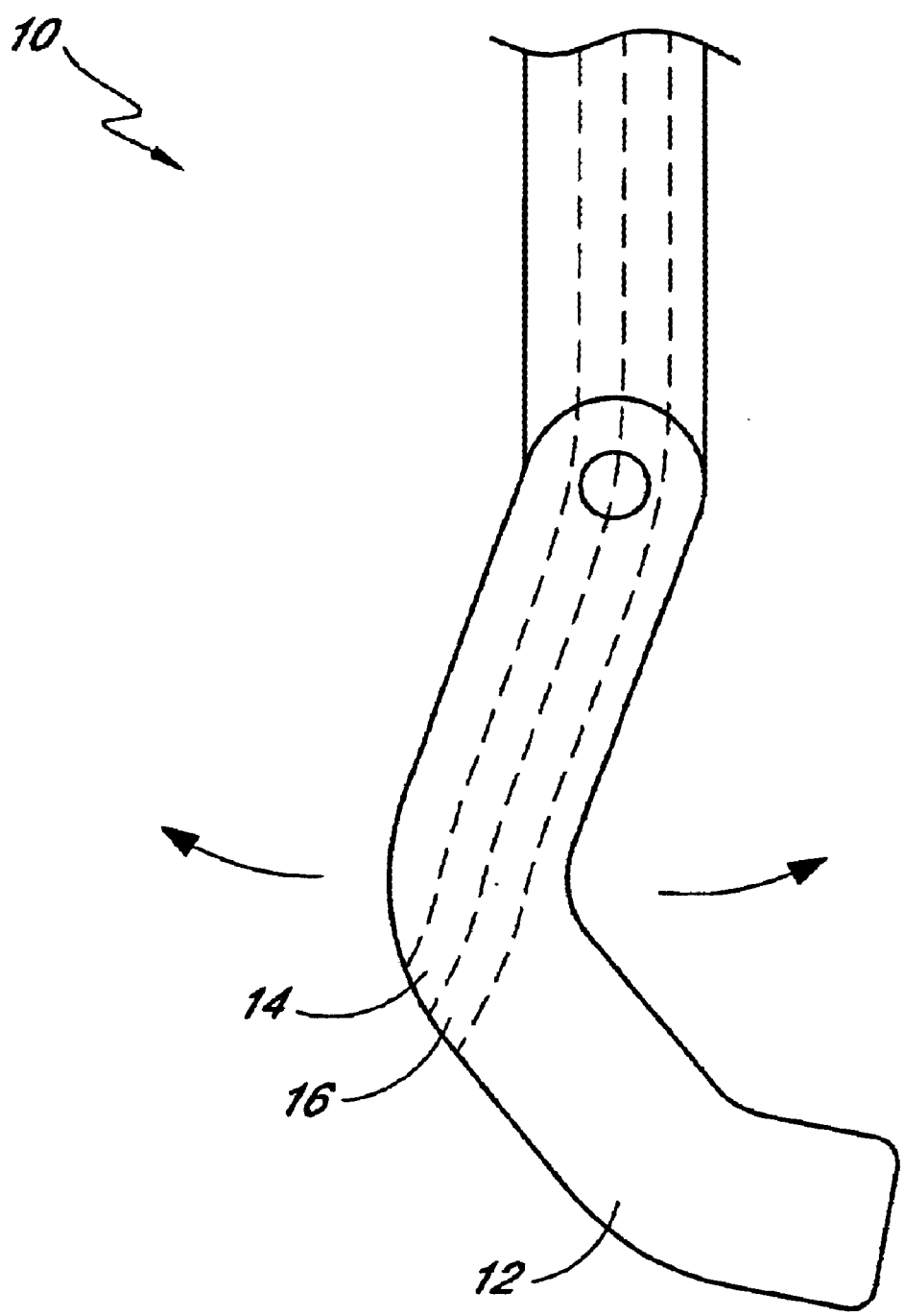
FIG. 1 illustrates the tip of a nerve root retractor which may advantageously be used in performing minimally invasive disc repair.

Embodiments of the invention will now be described with reference to the accompanying Figure wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

A minimally invasive disc repair using a posterior approach may include the following operations. A standard laminotomy incision, no more than 12 mm in length and the introduction of an expandable cannula down to the lamina of the involved disc pathology. The cannula is anchored when the tip is over the lamina and is expanded to 1.5 to 2 times its initial circumference. Additional expansion can be achieved by introducing a second expandable cannula that has an original circumference just under that of the expanded first cannula. Expanding the second cannula may produce a total expansion of approximately double or more of the circumference of the originally introduced un-expanded first cannula with myofascial soft tissue tension and the direct pressure of the expanding cannula. Various forms of expandable cannulas may be utilized. For example, suitable expandable cannulas are described in U.S. Pat. Nos. 5,961,499 and 3,788,318. The entire disclosures of these patents is hereby incorporated by reference in their entireties.

In one embodiment, the cannula includes integral fiber optics to assist in illuminating the surgical field. A clear visualization of the lamina will be available through the second expanded cannula, and a partial laminotomy can be performed.

After removing bone and ligament, the nerve root and thecal sac will be exposed. Using a flexible retractor, the tip of which is illustrated in FIG. 1, the thecal sac and nerve root can be retracted over. As shown in FIG. 1, the retractor 10 incorporates an angulating tip 12 which is made from non-conducting material, preferably non-conductive of both electricity and heat. This helps prevent thermal or electrical injury to the thecal sac and nerve root during procedures involving the application of electrical energy and/or heat such as RF coagulation and/or resection.

The retractor advantageously includes an internal lumen 14 for fiber optic illumination and imaging, as well as a lumen 16 for suction. Some embodiments of retractors with integral fiber optic illumination are described in U.S. Pat. Nos. 5,035,232 and 5,520,611, the entire disclosures of which are hereby incorporated by reference in their entireties. It is advantageous for the tip of the retractor 10 to also be expandable similar to the cannula so that maximum retraction can be achieved after the retractor is adjacent to the nerve root. The capabilities of the retractor for expansion, suction, illumination, and retraction can be accessed with triggers on the retractor handle. In those disk herniations in which the fragment may be between the nerve root and the thecal sac in its axilla, such retraction may prove to be beneficial for an abnormal anatomy such as a conjoint root, and the retractor described above would serve as a much more versatile means of obtaining operative visualization and retrieval of disk material in a safe manner.

With the fiber optic illumination, the disc space can be directly visualized, and disc pathologies identified and precisely located. In some advantageous embodiments, the retractor 10 is also provided with an anchoring spike so that the retractor can be fixed to the posterior vertebral body or adjacent soft tissues and allow for hands free retraction.

It will be appreciated that in some cases, extruded disc fragments will be identified. In these cases, the fragment can be removed with a standard pituitary rongeur. Following this procedure, the located fissure in the annulus can be repaired. In advantageous embodiments, this involves the application of heat to the fissure region to shrink the collagen of the annulus and close the fissure. Many different techniques may be used to apply heat to the fissure to shrink the collagen. For example, an endoscopically introduced thermal energy application device is described in U.S. Pat. No. 5,569,242 to Lax et al., the disclosure of which is hereby incorporated by reference in its entirety. In some cases, devices of this type may be introduced through the operating cannula to the fissure for the purpose of applying thermal energy thereto.

In some embodiments, these probes may include integral imaging components for accurate probe placement directly on an annular tear or other pathology. These imaging components may include ultrasound imaging devices, as well as optical coherence tomography and/or electrical coherence tomography apparatus. These devices may be used to accurately position the thermal energy application probe to the location of the fissure, tear, or nuclear protrusion of a disk, minimizing thermal damage to adjacent tissues.

In an especially advantageous embodiment, a light absorbing dye is introduced into the fissure opening through the operating cannula. Two possible dyes suitable for this use are indigo carmen and methylene blue. Another possibility is indosidin green. After application of the dye, illumination applied to the fissure area will selectively heat the dye to a greater extent than other areas of the disc. This will be especially true if the illumination is primarily in a wavelength band which is preferentially absorbed by the dye. As the dye heats, thermal energy will be transferred to the disc to heat and shrink the collagen as desired. Laser light is one advantageous method of illumination, although non-coherent light sources could also be utilized. Glycoadhesive proteins may be added to the dye to further help seal an annular tear or fissure during this process. In the case of a disk herniation or extruded fragment, the fragment can be removed, and instead of taking out nuclear material, the extruded fragment or fragments could be combined with glycoadhesive proteins and light absorbing dye to create a sealant for the annulus. The sealant may be applied to the disk with a probe, guided, if necessary, by the imaging methods described above, and laser light may heat the sealant to repair the disk.

It will also be appreciated that with the operating cannula in place, other beneficial procedures may be performed in addition to the fissure repair described above. Using a high speed burr, an internal laminoplasty, partial medial fasciectomy or foramenotomy may be performed prior to or after fissure repair. The burr may be provided with a moveable protective flap which covers the burr tip. The flap may be used for retraction to remove the thecal sac and nerve root from the area of resection. The burr may also be provided with integral lumens for either or both fiber optic illumination/imaging and suction.

The high speed burr is capable of performing an internal laminoplasty or foraminoplasty. In this technique, the device is placed through the expanding cannula into an interspinous region where the supraspinatus and infraspinatus ligament may have been removed, entering into the region between the spinal laminar junction and the ligamentum Clavum. What is then performed is an internal laminoplasty as if performing a subacromial decompression using an arthroscope. The high speed bur is then manually moved from right to left and it slowly resects the bone on the inner surface of the lamina, spinous process and facet joint.

Because of the embodiment of the high speed bur, which has a nerve root and thecal sac retractor, resection may be performed without damaging other tissues. The burs may also be attached with an irrigation system and suction that will allow the bone material and ligamentous detritus to be suctioned out of the operative portal. Such a high speed bur may also be attached to an operative table and the handle attached to an arm that is controlled by a computer, or by a robot, to meticulously resect appropriate amounts of bone in order to increase the cross sectional diameter at the stenotic level.

In order to obtain accurate measurements of the thickness of the lamina at various regions, optical coherence tomography, electrical coherence tomography or ultrasound can be utilized to assess the thickness of the resection. This minimally invasive spinal decompression for stenosis can also be performed with the burr entering into the neuroforamen since the nerve root retractor is also attached and can deflect the nerve root out of the way while the roof of the foramen is being decompressed adequately.

If desired, the movements of the high speed bur can be monitored under direct fluoroscopy or by direct fiberoptic visualization, using standard arthroscopy camera equipment. What can then be achieved is a single level or multi-level decompressive laminectomy and/or foramenotomy through very small mid-line incisions and having the patient go home within 48 hours, with x-rays showing a nearly intact spinous process and lamina at each level. This insures and minimizes the risks for iontogenic instability and will most likely decrease the need for lengthy posterior fusions with pedicel screws.

The above described techniques thus allow for disc fissure repairs without risk of damage to neighboring structures and tissues, and further allow for the surgical treatment of pathologies such as spinal stenosis, congenital spinal stenosis, neural foraminal stenosis, and ligamentum flavum hypertrophy. Thus, disc herniations ranging from a subligamentous bulge to an extruded free fragment, annulus fissures, and central or neural foraminal stenosis can be addressed with the above techniques at the same time with minimally invasive surgery.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of treating a disc pathology comprising:
    making a posterior surgical incision to expose a portion of a patient's spine;
    inserting an expandable cannula into said incision;
    expanding said cannula;
    inserting a retractor into said cannula;
    retracting a portion of a nerve;
    selectively applying a light absorbing dye only to a specific area localized near a previously visualized disc pathology; and
    thermally shrinking annular collagen by applying thermal energy to said disc annulus without applying a damaging amount of heat to said nerve by directing light to said light absorbing dye so as to selectively heat said dye.

2. The method of claim 1, comprising applying sealant to said specific area.

3. The method of claim 1, wherein said dye comprises one or more dyes selected from the group consisting of indigocarmine, methylene blue, and indosidin green.

4. The method of claim 2, comprising applying a mixture of sealant and light absorbing dye.

5. A method of treating a disc pathology comprising:
    making a surgical incision to expose a portion of a patient's spine;
    inserting a cannula into said incision;
    inserting a retractor into said cannula;
    retracting a portion of a nerve;
    selectively applying a mixture of light absorbing dye and protein sealant to a portion of a disc; and
    thermally shrinking annular collagen by applying thermal energy to said disc annulus without applying a damaging amount of heat to said nerve by directing light to said mixture so as to selectively heat said dye.

* * * * *